United States Patent [19]

Oba

[11] Patent Number: 4,724,536
[45] Date of Patent: Feb. 9, 1988

[54] INSTRUMENT TO MEASURE FLUORESCENCE WHICH HAS OCCURRED IN A SAMPLE STIMULATED BY X RAYS

[75] Inventor: Koichiro Oba, Hamamatsu, Japan

[73] Assignee: Hamamatsu Photonics Kabushiki Kaisha, Hamamatsu, Japan

[21] Appl. No.: 830,687

[22] Filed: Feb. 18, 1986

[30] Foreign Application Priority Data

Feb. 19, 1985 [JP] Japan .................................. 60-31076

[51] Int. Cl.[4] .......................................... G01N 23/223
[52] U.S. Cl. ...................................... 378/44; 378/119; 378/45
[58] Field of Search ........................ 378/45, 44, 119, 1; 250/458.1

[56] References Cited

U.S. PATENT DOCUMENTS 3,991,309  11/1976  Hauer ..................................... 378/72
4,435,828  3/1984  Epstein et al. ........................ 378/49

FOREIGN PATENT DOCUMENTS 0213512  9/1984  Fed. Rep. of Germany ......... 378/44

OTHER PUBLICATIONS

*Review of Scientific Instruments*, vol. 56, No. 6, Jun. 1985, pp. 1187–1194.

Okano, K., Nakagome, Y., Kawase, Y., Uehara, S., Nakano, Y., Kanda, K. and Shibata, T.; "An Automatic Irradiation Apparatus With On-Line Measurement System For The Study of Short-Lived Activities", Nuclear Instruments and Methods, 104(1972) pgs. 13–19.

Forsyth, J.M. and Frankel, R.D.; "Experimental Facility for nanosecond time-resolved, low angle x-ray diffraction experiments using a laser-produced plasma source"; Rev.Sci.Instrum.55(8), August 1984; pgs. 1235–1242.

Bialkowski, J. and Schoeps, W., "Constant Fraction Discriminator With Automatic Adjustment of Optimal Triggering Level and Automatic Suppression of AC and DC Input Interference Signals"; Nuclear Instru. & Methods in Physics Research, 228 (1984) pp. 110–117.

*Primary Examiner*—Carolyn E. Fields
*Assistant Examiner*—Joseph A. Hynds
*Attorney, Agent, or Firm*—Spencer & Frank

[57] ABSTRACT

An instrument measures fluorescence which has occurred in a sample stimulated by X rays. The instrument consists of a laser device, an X-ray pulse generation tube excited by the laser pulse from the laser device, a light sensor for detecting fluorescence in the sample, a reference timing pulse generator, a time-to-voltage converter to indicate the time of fluorescence and a multichannel analyzer to sum the frequency of times that the designated voltage is issued from the time-to-voltage converter in each voltage level during measurement.

12 Claims, 3 Drawing Figures

INSTRUMENT TO MEASURE FLUORESCENCE WHICH HAS OCCURRED IN A SAMPLE STIMULATED BY X RAYS

BACKGROUND OF THE INVENTION

The present invention relates to an instrument for measuring fluorescence which has occurred in a sample excited by X rays, and for measuring the life time of the fluorescence.

Well known is an instrument for measuring the property of fluorescence which has occurred in a material which is exposed to and excited by X rays so as to test the properties of materials and/or compositions.

An X-ray generation device which has been developed for medical applications is used to stimulate samples in the measuring instrument.

The pulse width of the X-ray pulse generated by the X-ray generation device, is at least 10 ns. The life time of fluorescence which occurs in a sample material is usually of the order of 100 ps to 10 ns. The pulse width of the X-ray pulse generated by the X-ray generation device is much greater than that required for measuring the life time of the fluorescence.

In addition, the pulse width of the X ray pulse generated by the Synchrotron which has recently been used is of the order of 100 ps.

Measuring instruments suitable for measuring still shorter fluorescence life times are still required in some fields. No X-ray source, however, is on the market for measuring such a short life time as described above.

The objective of the present invention is to solve this problem by utilizing an X-ray pulse train with an extremely short pulse width of 10 ps or less which can only be obtained by this new type of X-ray pulse tube exposed to a coherent light pulse train with an extremely short duration time which is generated from a laser tube.

The objective of the present invention is to provide an instrument for measuring fluorescence which has occurred in a sample excited by X-ray pulses with an extremely short duration time which has never been measured by any other conventional measuring instruments.

SUMMARY OF THE INVENTION

The instrument for measuring fluorescence which has occurred in a sample excited by X rays in accordance with the present invention consists of a laser device to generate a laser pulse train with an extremely short duration time, an X-ray pulse generation tube to generate an X-ray pulse train with an extremely short duration time responding to the laser pulse train, a light sensor for detecting fluorescence which can issue an output voltage when fluorescence with an intensity of greater than the threshold has occurred in a sample excited by an X-ray pulse train generated by the X-ray pulse generation tube, a reference timing pulse generator to generate the reference timing pulses synchronizing with a laser pulse train generated by the laser device, a time-to-voltage converter to generate a voltage corresponding to the time measured from generaton of the reference timing pulse to generation of the light sensor output and a summing device to sum the frequency of times that the designated voltage is issued from the time-to-voltage converter in each voltage level.

DESCRIPTION OF THE PREFERRED EMBODIMENT

Figure 1:
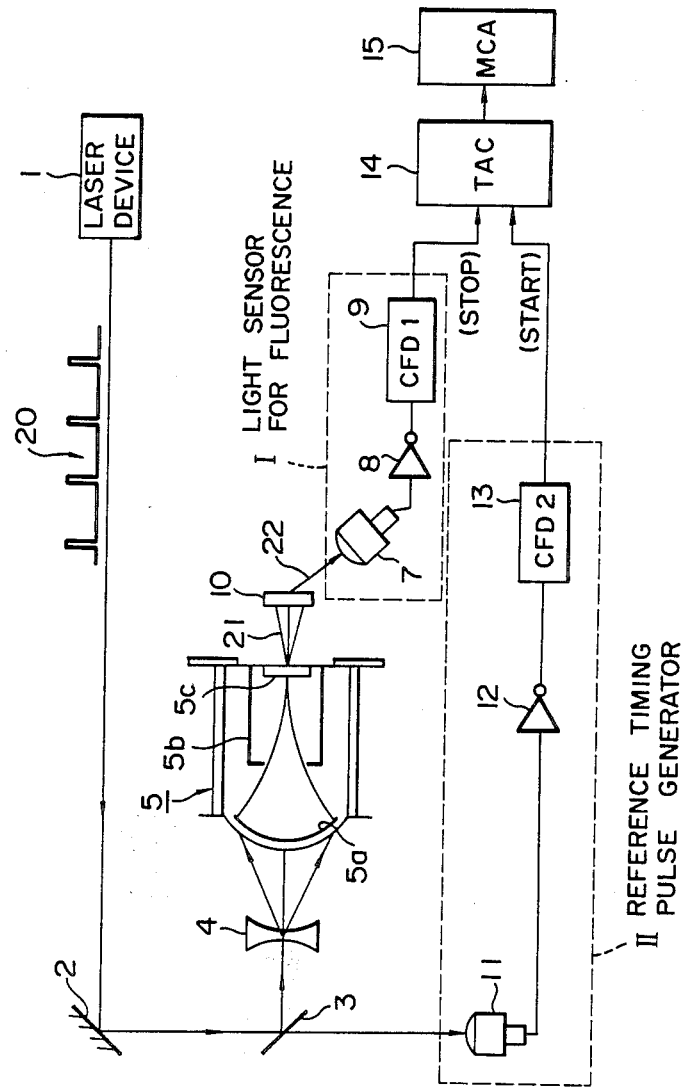
FIG. 1 shows a block diagram of the instrument for measuring fluorescence which has occurred in a sample excited by X-ray pulse train in accordance with the present invention.

The present invention will be described in detail hereafter referring to the drawings.

FIG. 1 shows a block diagram of the instrument for measuring fluorescence which has occurred in a sample excited by an X-ray pulse train.

A laser pulse train 20 with an extremely short duration time is generated by laser device 1.

The laser pulse train 20 is reflected from total reflection mirror 2 and then branches into two routes via half mirror 3.

The light beam reflected from half mirror 3 is magnified by concave lens 4 and incident on photocathode 5a of X-ray pulse generation tube 5. X-ray pulse generation tube 5 consists of the photocathode 5a, focusing electrode 5b and X-ray target 5c of the transparent type. The generating voltages are supplied from an external power supply (not shown) to X-ray pulse generation tube 5. Photoelectrons generated by a laser pulse train incident on photocathode 5a of X-ray pulse generation tube 5 are used to generate X-ray pulse train 21 synchronizing with the laser pulse train 20 while striking X-ray target 5c.

Such a material as Ti, Al, Cu or Ni can be used for fabricating the X-ray target. This type of material can be used to generate a characteristic X ray which is proper to a specific material, and to generate a continuous spectrum due to BREMSSTRAHLUNG.

Figure 3:
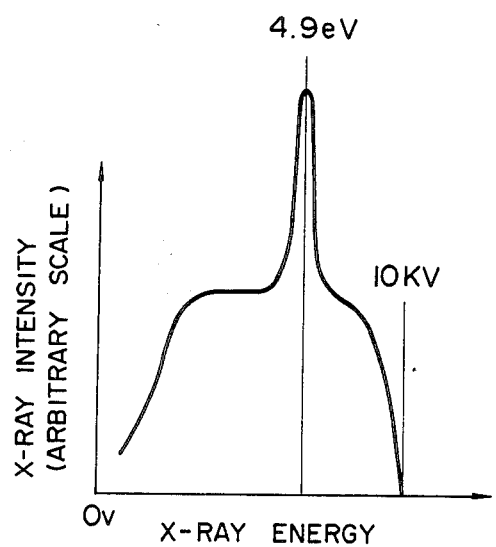
FIG. 3 shows a graph of the X-ray energy intensity distribution for the X ray pulse tube.

FIG. 3 shows an X-ray energy intensity distribution obtained when the X-ray pulse generation tube made with a Ti target is operated at an acceleration voltage of 10 kV.

X-ray pulse train 21 is an X-ray pulse train with an extremely short duration time of 10 ps or less which has never been obtained.

Sample 10 is stimulated and excited by the X-ray pulse train 21 and then fluorescence with an extremely low intensity can occur.

The lifetime of fluorescence depends on the type of material on which fluorescence has occurred, and it may range from 100 ps to 10 ns.

The intensity of light due to fluorescence is decreased to such a quantity as a single photon energy level, and it can be detected by light sensor I for fluorescence. When the fluorescence is detected in the light sensor I, light sensor I issues an output.

Light sensor I consists of high speed photodetector 7, amplifier 8 and first constant fraction discriminator (CFD1) 9.

Reference timing pulse generator II generates a reference timing pulse each time a light pulse passes through the half mirror 3. Reference timing pulse generator II consists of high-speed light detector 11, amplifier 12 and second constant fraction discriminator (CFD2) 13.

The start signal input terminal of time-to-voltage converter (TAC) 14 is connected to the output terminal of the reference timing pulse generator II, and the stop signal input terminal of the time-to-voltage converter (TAC) is connected to the output terminal of the light sensor I.

Time-to-voltage converter (TAC) 14 generates a voltage signal whose value corresponds to the time measured from generation of the reference timing pulse to generation of the output signal of light sensor I each time a light pulse is issued from the laser device.

Multichannel analyzer (MCA) 15, operated as a summing device, is used to draw a decay curve of the fluorescence when the outputs of the time-to-voltage converter (TAC) 14 are summed.

Figure 2:
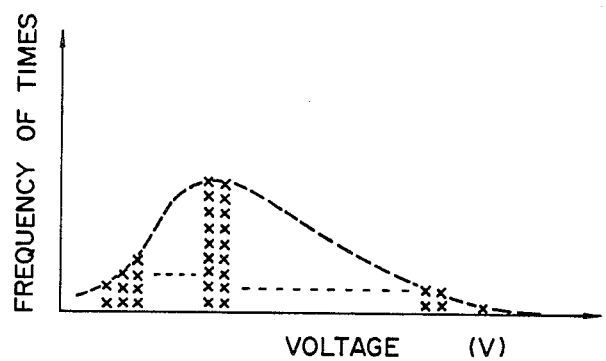
FIG. 2 shows a graph of data measured by the instrument.

FIG. 2 shows a graph of the result of measurement.

The abscissa in FIG. 2 indicates output voltage V of time-to-voltage converter 14 and the ordinate indicates the frequency distribution obtained by repetitive measurements at each voltage.

The ordinate indicating the voltage corresponds to the time because the voltage and time have a one-to-one correspondence. Thus, the frequency curve in FIG. 2 indicates the time in fluorescence which is acquired by repetitive measurement of photons separately issued from the photocathode.

As described above, the instrument to measure fluorescence which has occurred in a sample stimulated by X rays uses an X-ray pulse generation tube which can generate an X-ray pulse train with an extremely short duration time when the X-ray pulse generated tube is stimulated and excited by the laser pulse train generated from the laser device. The sampel is thus excited by the repetitive X-ray pulses at high speed without any misexcitation.

The statistical method of measuring the profile of fluorescence can thus be done reliably.

This method permits the life time of fluorescence to be measured which has occurred in a sample stimulated by X-ray pulses, and it may spread out the field of applications in research and development.

What is claimed is:

1. An instrument for measuring fluorescence which has occurred in a sample stimulated by X-rays, comprising
    first means for generating a series of light pulses;
    second means for generating a series of X-ray pulses which impinge upon said sample when excited by the light pulses from said first means, the duration of each of said X-ray pulses being on the order of 10 ps or less;
    third means for sensing fluorescence emitted by said sample when an X-ray pulse generated by said second means impinges on said sample, said third means generating an output signal when said fluorescence exceeds a predetermined threshold level;
    fourth means for receiving the light pulses generated by said first means, said fourth means generating reference timing pulses synchronized with said light pulses;
    fifth means coupled to said third and fourth means, said fifth means generating a voltage corresponding to the time elapsing between the generation of a timing pulse by said fourth means and the generation of an output signal by said third means, wherein the output signal generated by said third means and the timing pulse generated by said fourth means are synchronously triggered by said light pulses; and
    sixth means for summing the frequency of times during measurement that a given voltage is generated by said fifth means at each voltage generated by said fifth means.

2. An instrument for measuring fluorescence as claimed in claim 1, wherein said sixth means is a multichannel analyzer.

3. An instrument for measuring fluorescence as claimed in claim 1, wherein said first means is a laser.

4. An instrument for measuring fluorescence as claimed in claim 1, wherein said second means is an X-ray pulse generation tube.

5. An instrument for measuring fluorescence as claimed in claim 4, wherein said X-ray pulse generation tube comprises a photocathode, a focusing electrode and a target, photoelectrons emitted by said photocathode when a light pulse impinges thereon being focused by said focusing electrode and exciting said target, whereby said X-ray pulses are emitted from said target.

6. An instrument for measuring fluorescence as claimed in claim 1, wherein said third means comprises a photodetector for receiving the fluorescence emitted by said sample and a first constant fraction discriminator connected to the output of said photodetector for generating said output signal.

7. An instrument for measuring fluorescence as claimed in claim 1, wherein said fourth means comprises a light detector for receiving the light pulses emitted by said first means and a second constant fraction discriminator connected to the output of said light detector for generating said timing pulses.

8. An instrument for measuring fluorescence as claimed in claim 1, wherein said fifth means comprises a time-to-voltage converter.

9. An instrument for measuring fluorescence which has occurred in a sample stimulated by X-rays, comprising
    a laser for generating a series of light pulses;
    an X-ray pulse generation tube for generating a series of X-ray pulses which impinge upon said sample when excited by the light pulses generated by said laser, the duration of each of said X-ray pulses being on the order of 10 ps or less;
    sensor means for sensing fluorescence emitted by said sample when an X-ray pulse generated by said X-ray pulse generation tube impinges on said sample, said sensor means generating an output signal when said fluorescence exceeds a predetermined threshold level;
    a reference timing pulse generating circuit for receiving the light pulses generated by said laser, said circuit generating reference timing pulses being synchronized with said light pulses;
    a time-to-voltage converter coupled to said sensor means and said reference timing pulse generating circuit, said converter generating a voltage corresponding to the time elapsing between the generation of a timing pulse by said reference timing pulse generating circuit and the generation of an output signal by said sensor means, wherein the output signal generated by said sensor means and the timing pulse generated by said reference timing pulse generating circuit are triggered by the same light pulse; and
    a multichannel analyzer for summing the frequency of times during measurement that a given voltage is generated by said time-to-voltage converter at each voltage generated by said converter.

10. An instrument for measuring fluorescence as claimed in claim 9, wherein said X-ray pulse generation tube comprises a photocathode, a focusing electrode and a target, photoelectrons emitted by said photocathode when a light pulse impinges thereon being focused by said focusing electrode and exciting said target, whereby said X-ray pulses are emitted from said target.

11. An instrument for measuring fluorescence as claimed in claim 9, wherein said sensor means comprises a photodetector for receiving the fluorescence emitted by said sample and a first constant fraction discriminator connected to the output of said photodetector for generating said output signal.

12. An instrument for measuring fluorescence as claimed in claim 9, wherein said reference timing pulse generating circuit comprises a light detector for receiving the light pulses emitted by said first means and a second constant fraction discriminator connected to the output of said light detector for generating said timing pulses.

* * * * *